(12) United States Patent
Burchman

(10) Patent No.: US 8,073,517 B1
(45) Date of Patent: *Dec. 6, 2011

(54) SYSTEM AND METHOD FOR MEASURING BLOOD CONSTITUENTS USING A CATHETER

(75) Inventor: Corey A. Burchman, Hanover, NH (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/791,843

(22) Filed: Jun. 1, 2010

Related U.S. Application Data

(63) Continuation-in-part of application No. 11/565,321, filed on Nov. 30, 2006, now Pat. No. 7,729,735.

(51) Int. Cl.
*A61B 5/00* (2006.01)
(52) U.S. Cl. ........................................... 600/341
(58) Field of Classification Search .................. 600/339
See application file for complete search history.

(56) References Cited

U.S. PATENT DOCUMENTS

| 7,246,620 B2 * | 7/2007 | Conroy, Jr. ............. 128/205.11 |
| 2002/0120204 A1 * | 8/2002 | Pfeiffer et al. ................. 600/505 |
| 2006/0155258 A1 * | 7/2006 | Rogers et al. ................. 604/508 |

OTHER PUBLICATIONS

Paoletti, et al, "Observations on the Implantation Technique and its Complications", "Central Venous Catheters", 2005, pp. 555-560, vol. 71, No. 9, Publisher: Minerva Anestesiol, Published in: Perugia, Italy.
Reinhart, et al, "Continuous Central Venous and Pulmonary Artery Oxegen Saturation Monitoring in the Criticall Ill", "Original", Jun. 9, 2004, pp. 1572-1578, Publisher: Intensive Care Med, Published in: Jena, Germany.
White, et al , "Continuous Jugulare Venous Oximetry in the Neurointensive Care Unit-A Brief Review", "Department of Anesthesia", Dec. 7, 2001, pp. 623-629, vol. 49, No. 6, Publisher: Neuroanesthesia and Intensive Care, Published in: Toronto, Canada.
Bloos, et al, "Venous Oximetry", "Physiological Note", Jun. 4, 2005, pp. 911-913, vol. 31, Publisher: Intensive Care Med, Published in: Jena, Germany.
Reinhart, et al, "The Value of Venous Oximetry", "NCBI", Jun. 11, 2005, p. 1, Publisher: PubMed, Published in: USA.
Cathelyn, et al, "Sv02 Monitoring: Tool for Evaluating Patient Outcomes", "Sv02 Monitoring: Tool for Evaluating Patient Outcomes", Mar. 1998, pp. 58-63, vol. 17, No. 2, Publisher: Clinical Deminesions, Published in: Tennessee, USA.
Crawford, et al, "Pulse Oximetry", "Dartmouth Biomedical Libraries", Apr. 2006, Publisher: Up to Date.

* cited by examiner

*Primary Examiner* — Nicholas D Lucchesi
*Assistant Examiner* — Jason Flick
(74) *Attorney, Agent, or Firm* — William A. Loginov, Esq.; Loginov & Associates, PLLC

(57) ABSTRACT

A system and method for confirming the proper placement of a penetrating catheter into a venous region using principles of oximetry in which blood is subjected to light of a plurality of wavelengths and detected for absorption levels. The result is analyzed by a processor and the level oxygen saturation of the blood is indicated. The characteristic level of saturation informs the practitioner whether oxygenated arterial blood is present due to an inadvertent puncture. The catheter is introduced using an introduction needle and thereafter removed to allow blood to communicate with sensing elements that consist of a light-emitter and opposed photodetector. Light in the infrared and visible red wavelengths can be provided by separate LED units. Aspiration of blood through the catheter by an attached syringe allows the processor to compute the level of oxygen saturation or other blood constituent, based upon detected light absorption of passing blood.

30 Claims, 10 Drawing Sheets

SYSTEM AND METHOD FOR MEASURING BLOOD CONSTITUENTS USING A CATHETER

RELATED APPLICATIONS

This application is a continuation-in-part of U.S. patent application Ser. No. 11/565,321, filed Nov. 30, 2006, entitled SYSTEM AND METHOD FOR VENOUS OXIMETRY USING A CATHETER, the entire disclosure of which is herein incorporated by reference.

FIELD OF THE INVENTION

This invention relates to the accurate placement of central venous catheters within a central venous compartment of the body, and more particularly to novel techniques described herein employing venous oximetry to facilitate such accurate placement.

BACKGROUND OF THE INVENTION

Central venous catheters (CVCs) are placed in excess of ten million times annually in the United States. Access to the central venous compartment (e.g. Great veins interconnected to the cardiopulmonary system) by such CVCs is acquired to allow for the administration of fluids, nutritional support and medications that are not necessarily suitable for peripheral venous delivery. CVCs may also be employed to access the central venous compartment to enable measurement of certain hemodynamic variables that are otherwise unobtainable by accessing peripheral veins, or by non-invasive techniques.

There are certain risks associated with the insertion of CVCs, which include pneumothorax (the collection of gas in the space surrounding the lungs), hemothorax (the collection of blood/fluid in that space), failed insertion and inadvertent arterial puncture. Where a CVC is inserted via an internal jugular venous approach, the most commonly described, and very dangerous, complication is inadvertent carotid artery puncture. This is the second most commonly described complication in the subclavian venous approach.

There are several current approaches to percutaneous CVC placement. In Seldinger's Method, the skin is prepped, and under sterile conditions, the percutaneous vein is punctured with a thin needle (for example, 20-gauge, or approximately 1 mm in outer diameter). A flexible guide wire is then introduced through the needle lumen and the needle is removed. A larger diameter dilator is then guided over the wire to facilitate passage of a larger bore (for example, 8-9 French, or up to approximately 3-4 mm in outer diameter). An alternate insertion approach entails venipuncture by the thin needle followed by guidewire placement. The larger-diameter catheter is then inserted while the guide wire is removed. Other approaches may also be employed, depending upon the type of device being inserted. Each of these approaches requires perforation of the target vessel using a needle.

While inadvertent arterial puncture using the introducing needle is usually an obvious condition, because of the arterial bleeding that results from even a small puncture, it often is not. Subsequent placement of a large-bore catheter or introducer into the carotid artery or another arterial structure can have lethal consequences. There have been reports of thromboembolic sequelae (broken blood clots leading to stroke, embolism, etc.) as a result of such punctures. Once damage has occurred, the neck or other region may require surgical exploration to assess and repair the damage. This can lead to further risk, expense and delays in attending the initial surgical problem which necessitated the CVC insertion.

One approach to reducing the risk in placing a percutaneous CVC is to monitor the insertion using interoperative imaging with an ultrasound or another type of internal imaging device. In some situations, radiopaque markers on the catheter/needle can be employed to assist guidance under fluoroscopy or similar scanning techniques. However, the surrounding structures of the neck may obscure a clear view of the target vein. Thus, while the needle appears clearly, the walls of the vein may not. Hence, reports of inadvertent carotid artery puncture, subsequent arterial cannulation and morbidity persist, even when employing interoperative imaging.

Another possible approach to reducing the risk of arterial cannulation is to employ a scout needle, in which a short, 20-gauge catheter is operatively connected to a pressure transducer before insertion of a guidewire. A variation or differential in pressure may indicate a A technique that more reliably ensures the needle is in communication with the vein, and not an artery is highly desirable.

SUMMARY OF THE INVENTION

This invention overcomes the disadvantages of the prior art by providing a system and method for confirming the proper placement of a penetrating catheter into a venous region without undesirable arterial cannulation using principles of oximetery in which blood form the penetrated region is subjected to light of a plurality of wavelengths and detected for absorption levels. The result is analyzed by a processor and the level oxygen saturation of the blood is indicated. The characteristic level of saturation informs the practitioner whether oxygenated arterial blood is present due to, for example, an inadvertent puncture. Other measurements of blood constituents can also be obtained using varying wavelengths, such as for determining the level of solutes, electrolytes, complex molecules, and pharmacologic agents.

In an illustrative embodiment, the catheter is introduced using an introduction needle. Thereafter the needle is removed to allow blood to communicate with sensing elements that consist of a light-emitting LED (or other light source of characteristic wavelength) array and opposed photodetector. In an illustrative embodiment, light in the infrared and visible red wavelengths can be provided by separate LED units within the overall array. Aspiration of blood through the catheter by an attached syringe allows the processor to compute the level of oxygen saturation or other blood constituent, based upon detected light absorption of passing blood, using the Beer-Lambert law. The sensing elements can be miniaturized so as to be located in the distal tip of the catheter, and can be operatively connected to an external connector via embedded leads. The processor connects to the leads through cables and the like, and also connects to a display. An optional non-invasive co-oximeter can also be connected to the processor to provide a compared value for oxygen saturation or other blood constituent of arterial blood by which the readout of the display is calibrated. The catheter is approximately 1 mm in inner diameter in an illustrative embodiment. Following confirmation of a safe location, it can guide a conventional guide wire and is then removed, leaving the guidewire in place in the vein. A larger diameter CVC can then be safely inserted into the vein over the guidewire, which is then, itself, removed leaving the CVC in place.

In further embodiments, the catheter can include a bulb that supports externally mounted sensing elements into which blood from the vein is aspirated. The external sensing elements can measure absorption of light by the blood passing between the light emitter and the photodetector and determining a level of blood constituents, including solutes, elecvtrolytes, complex molecules, and pharmacologic agents, among others. The sensing elements can be larger scale in such an embodiment. Alternatively, an elongated flexible version of the catheter with either internal or external sensing elements can be employed. It is adapted to be guided into a more remote location within the vascular system using conventional guiding techniques.

BRIEF DESCRIPTION OF THE DRAWINGS

The invention description below refers to the accompanying drawings, of which.

DETAILED DESCRIPTION

Figure 1:
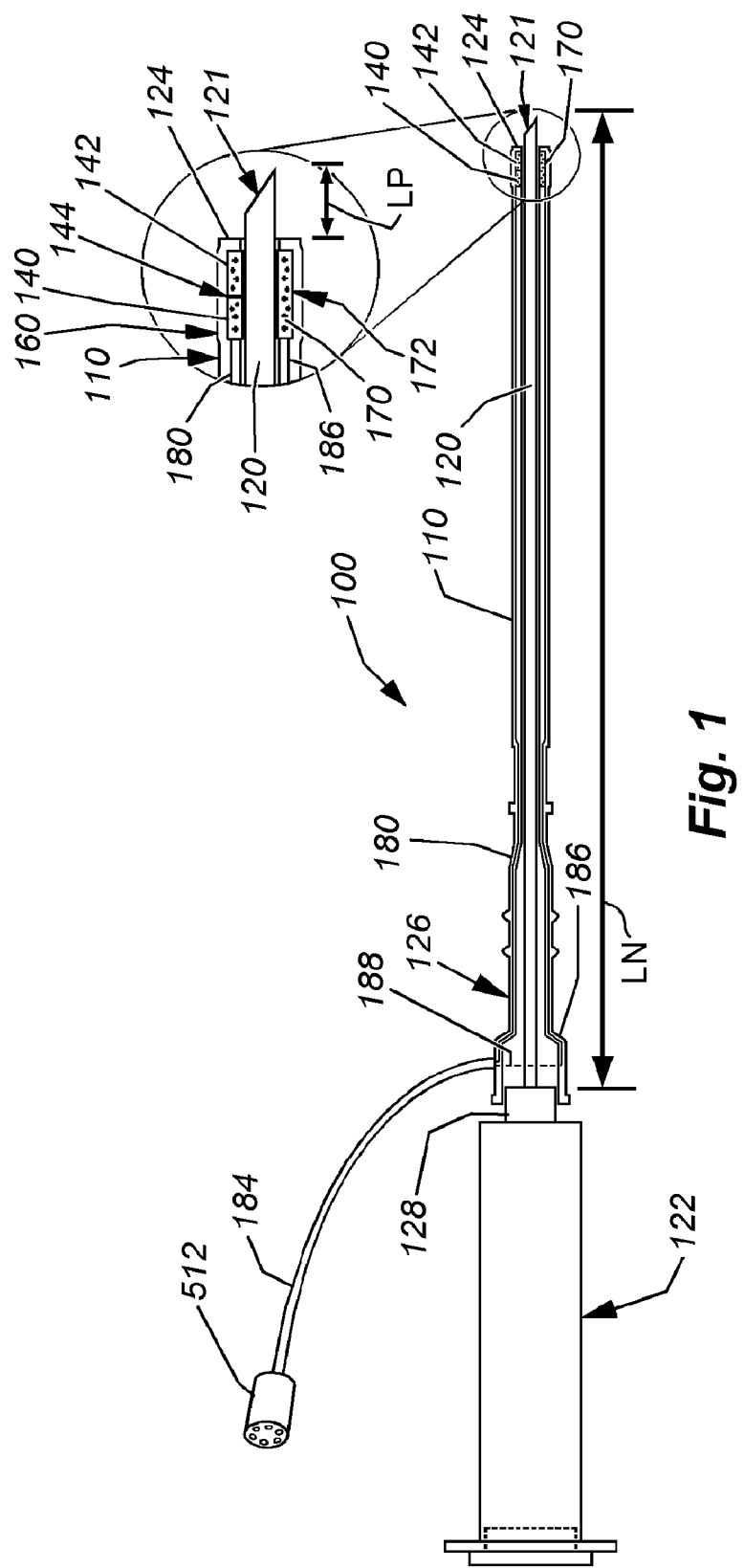
FIG. 1 is an exposed side view of a central venous oximetry catheter according to an illustrative embodiment of this invention.

A. Oxygenation of Hemoglobin and Principles of Oximetry

The vast majority of oxygen in blood is carried on the hemoglobin molecule with minimal amounts dissolved in the plasma. Due to the unique characteristics of hemoglobin, arterial blood and venous blood generally carry substantially differing amounts of oxygen. For example, in a healthy body arterial blood oxygenated hemoglobin (oxyhemoglobin) is between 96-100% of the total hemoglobin concentration. Conversely, venous blood (deoxyhemoglobin) typically reads a maximum saturation in the 80 percent range. In an unhealthy body, venous blood may read in the 60 percent range. Thus, there is a clear delineation between concentrations of oxygenated hemoglobin in venous versus arterial blood.

The measurement of blood oxygen levels though use of oximetry is well-known. One such device is the pulse oximeter, which non-invasively detects the subject's blood-oxygen level. The pulse oximeter operates on the principle of the Beer-Lambert law. Briefly, the law states that the absorption of light of a given wavelength passing through a non-absorbing solvent, which contains an absorbing solute, is proportional to the product of the solute concentration, the light path length and an extinction coefficient. The law can be expressed as:

$$A = bc$$

where A is absorbance (no units, since $A = \log_{10} P_0/P$); is the molar absorbtivity with units of L mol$^{-1}$ cm$^{-1}$; b is the path length of the sample—that is, the path length of the vessel in which the sample is contained (typically in millimeters, centimeters, etc.); and c is the concentration of the compound in solution, expressed in mol L$^{-1}$.

A pulse oximeter is placed in contact with skin containing sufficient blood vessels (a finger, for example), light of at least two wavelengths is transmitted so as to pass through the blood vessels. Typically the oximeter has a pair of small light-emitting diodes (LEDs) facing a photodiode through a translucent part of the patient's body, usually a fingertip or an earlobe. One LED is red, with wavelength of 660 nm, and the other is infrared, 910 nm. Absorption at these wavelengths differs significantly between oxyhemoglobin and deoxyhemoglobin. In particular, oxyhemoglobin absorbs maximally in the infrared band (850-1000 nm), while deoxyhemoglobin absorbs light maximally in the visible red band (600-750 nm). By employing the Beer-Lambert law in association with the detected values for absorption, the ratio of the absorption of the red and infrared light the oxy/deoxyhemoglobin ratio can be calculated using known techniques.

In non-invasive, pulse oximetry the monitored signal bounces in time with the heart beat (hence, the term pulse oximeter) because the arterial blood vessels expand and contract with each heartbeat. By examining only the varying part of the absorption spectrum (essentially, subtracting minimum absorption from peak absorption), an interconnected monitor can ignore other tissues or other intervening materials (for example, nail polish), and discern only the absorption caused by arterial blood.

More recently, special spectrophotometric oximetry catheters have been developed that allow in vivo measurement of central venous blood oxygenation. They can be employed for a variety of purposes including the continuous monitoring of brain blood-oxygen saturation (also termed SjVO$_2$) via insertion into the jugular bulb. In general they employ fiberoptic wave guides in communication with an external base unit to perform oximetric monitoring of blood near the catheter's distal end. Two or more waveguides transmit the appropriate, corresponding wavelengths of light from the base while another light waveguide receives the modulated (absorbed) light and transmits it back to the base for analysis. Such monitoring a techniques, and commercially available oximetry systems, are discussed in *Continuous jugular venous oximetry in the neurointensive care unit—a brief review*, Canadian Journal of Anesthesia, 2002 (pages 623-629). These SjVO$_2$ monitoring catheters are designed for permanent insertion into the patient's central vascular system and can be of relatively large-diameter, similar is size and form to other CVCs. Hence, the insertion of monitoring catheters dictates the same initial puncture and guidance procedures, and therefore entails the same risks of inadvertent arterial puncture, as with the insertion other types of CVCs.

B. The Oximetry Catheter and Insertion/Use Procedure

FIG. 1 details an oximetry catheter assembly 100 in accordance with an illustrative embodiment of this invention. The catheter assembly consists of the outer oximetry catheter 110 (termed hereinafter generally, the "catheter") and an inner introduction needle 120, over which the catheter 110 resides, in relatively close conformance. The distal/sharp end 121 of needle 120 projects beyond the distal end 124 of the catheter 110 a distance LP of approximately 2-4 millimeters. The needle 120 includes a conventional syringe body or hub 122 at its opposing proximal end. This body/hub 122 is suitable for grasping and manipulating the assembly 100 in the manner of a conventional introducer catheter. The catheter 110 includes its own proximal hub 126 that can be adapted to engage the distal end 128 of the needle hub 122 as shown. In this manner, a substantially fluid-tight seal is maintained between the hubs 122, 126. Note that the catheter hub 126 can be constructed to include a variety of external bases, flanges, side connections and other structures that facilitate its use in a particular procedure.

The needle 120 is substantially rigid and can be constructed from stainless steel or another biocompatible material in this embodiment. It is a 20-gauge (approximately 1 mm O.D.) needle in this embodiment. Other relatively thin-outer-diameter needle sizes are also contemplated. The needle 120 defines an overall length LN of between approximately 10 and 100 millimeters. The actual needle length is dependent upon the precise point of insertion of the needle, as some vascular bodies are more or less deeply located than others. The length should be defined so that the catheter hub 126 engages the external skin when the distal tip is positioned within the vein. The overall length of the catheter 110 is proportional to that of the needle, with appropriate allowance needle's distal end 121 to project slightly so as to allow it to puncture external tissue and the vascular wall (refer below).

Figure 4:
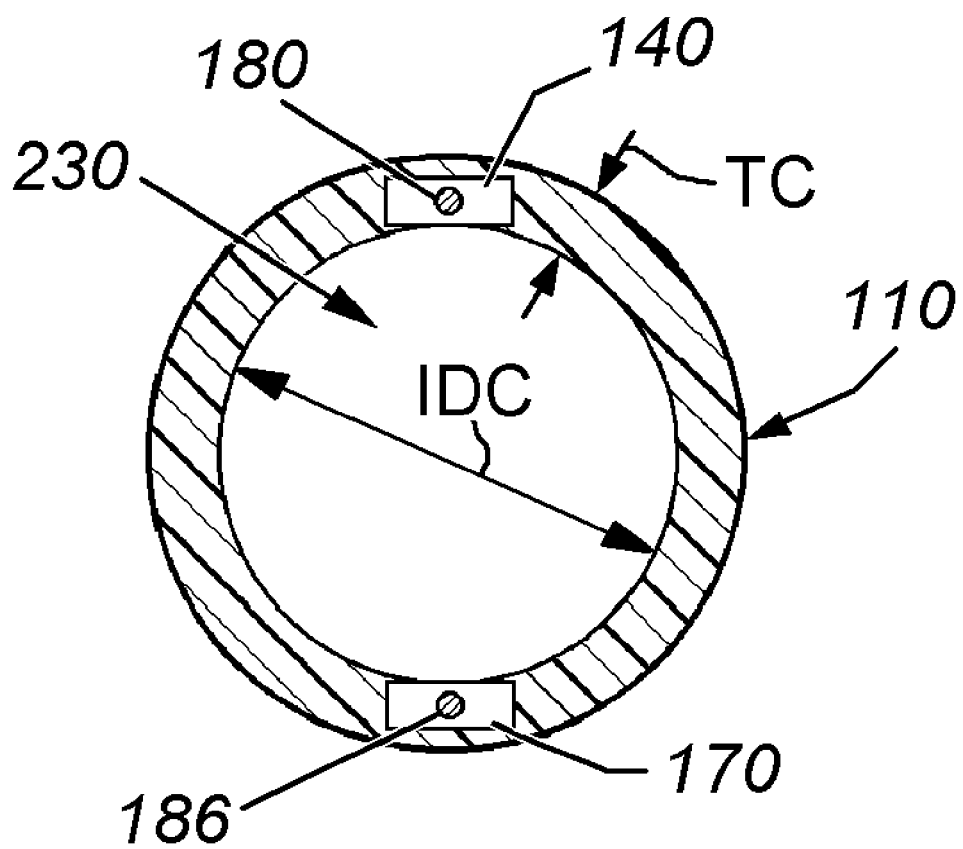
FIG. 4 is a cross section through the LED and sensor array taken along line 4-4 of FIG. 3.

With brief reference also to the cross section of FIG. 4, the catheter 110 is relatively thin. Its wall thickness TC can be approximately 100-200 microns in an illustrative embodiment. Other thicknesses are contemplated however. The catheter is constructed from an appropriate, typically polymeric, material, and can include low-friction surface coatings, such as PTFE along the interior and/or exterior surfaces. A variety of surface coatings that are generally known to those of ordinary skill can be employed.

The catheter inner diameter IDC allows it to closely conform to the outer surface of the needle 120. For a 20-gauge introduction needle, the inner diameter IDC is approximately 1 mm. This should be sufficient to accommodate a conventional catheter guidewire as described further below. The relatively thin wall thickness TC of the catheter 110 provides a low-profile that, in essence, enables its own distal end 124 to piggy-back on the needle distal end and pass through tissue without causing trauma as the needle's tip is driven inwardly/distally. In other words, the catheter's low-profile distal end 124 does not overly distend the surrounding tissue boundaries that are initially defined by the sharp needle tip.

Figure 2:
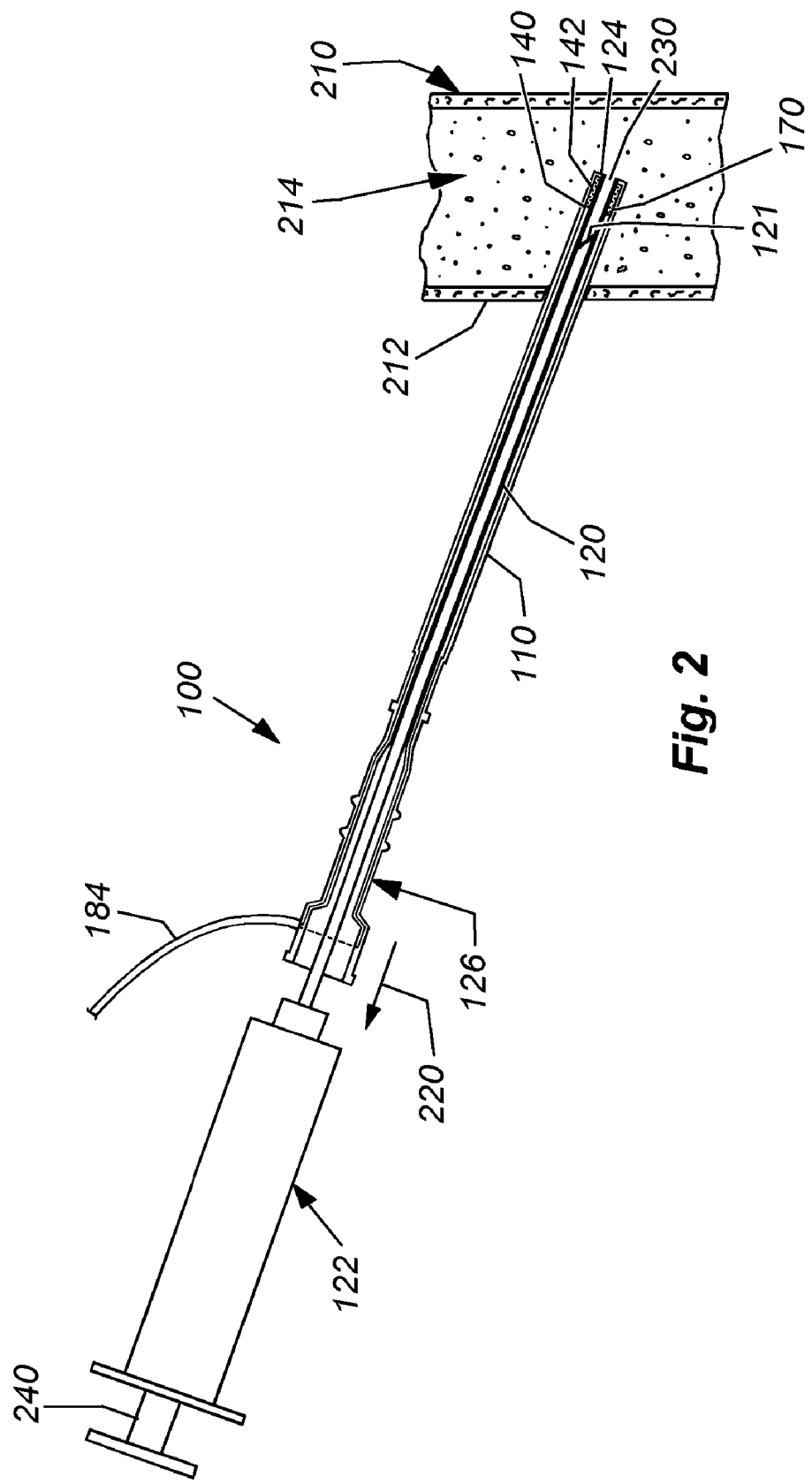
FIG. 2 is an exposed side view of the catheter of FIG. 1 showing the insertion thereof into a central venous region and the subsequent of an introduction needle associated therewith.

With reference also to FIG. 2, the insertion of the assembled needle 120 and catheter 110 into a central vascular region (for example, the jugular) 210 is further detailed in FIG. 2. The needle has been appropriately oriented and driven distally within a sterile field so as to puncture and pass through surrounding tissue and the vascular wall 212. Using ultrasound, or similar imaging techniques, the distal to has been guided to reside within the bloodstream 214. Within the bloodstream, the distal tip is communication with surrounding blood, containing deoxyhemoglobin. As shown, once properly positioned, the practitioner can grasp the catheter hub 126, holding it in place against the external skin, while withdrawing (arrow 220) the needle 120 via simultaneous grasping of the syringe body 122. The overlying catheter 110 remains in place within the vein 210 and its inner lumen 230 is now in fluid communication with the surrounding blood (214).

Notably, the distal end 124 of the catheter 110 includes at least two embedded light emitters 140, 142 (FIG. 1). Recent developments in micro-LED technology have rendered it possible to embed one or more micro-LEDs in an array unit 144 that is readily molded-into, or applied to the inner luminal wall of the catheter 110. At present, bright LEDs as small as 20 microns in diameter can be formed from gallium nitride (GaN) material in accordance with research conducted at Scotland's University of Strathclyde, Institute of Photonics. Larger micro-LEDs that conform to the needed form factor may be obtained from other sources. As shown, a luminal surface mounted array 144 is provided, which may slightly bulge the outer surface of the catheter's distal end when combined with the needle 120. The projection of his bulge 160 is still small enough to enable ready insertion of the assembly 100 into tissue.

Positioned in diametrical opposition (180 degrees) to the LED array 144 is a photodetector 170. The photodetector 170 resides on the luminal surface of the catheter and also forms a small, non-interfering bulge 172. The photodetector can comprise one or more photo-detecting cells that generate a variable voltage, current or other signal proportional to the intensity of received light within a given operating wavelength. The LEDs 140, 142 each emit at a characteristic wavelength—one in the infrared band (for oxyhemoglobin detection), and one in the visible-red band (for deoxyhemoglobin detection). The detector 170 is sensitive to both wavelengths.

The LEDs 140, 142 are connected to one or more leads 180 that pass proximally along, or within, the luminal wall to an external connector cable 184 mounted on the hub 126. The photodetector 170 is connected to a lead 186, which joins the cable 184 via a bridge 188 (shown in phantom). The leads 180, 186 and bridge 188 can be formed from thin metal, conductive ink, embedded metal or graphite powder, or another appropriate conductor of electricity. In certain embodiments, the catheter wall can be doped with conductive material to provide integral leads from the array 144 and photodetector 170 to the hub 126.

Figure 3:
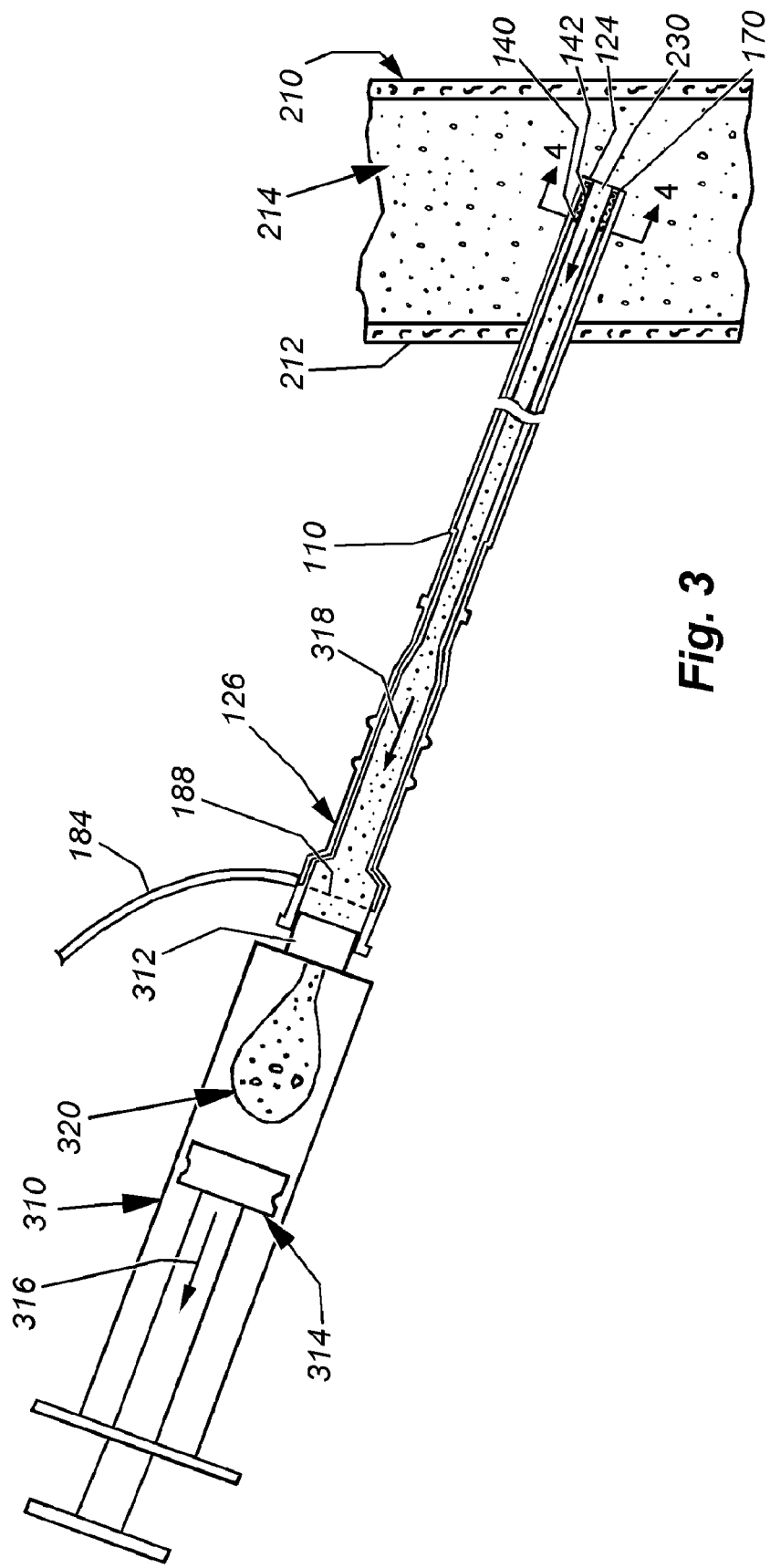
FIG. 3 is an exposed side view of the catheter of FIG. 1 showing the aspiration of blood from the central venous region to perform an oximetry function.

With reference to FIG. 3, the catheter is now in place with the distal tip 124 located within the bloodstream 214 of the (supposed) venous region, and the needle 120 is completely withdrawn. The distal end 312 of a new syringe 310, without needle covering the array 144 and photodetector 170, is attached to the proximal end of the catheter hub 126. The syringe can be a conventional 5 ml syringe in this embodiment. This forms a substantially fluid-tight seal therebetween. The plunger 314 of the syringe 310 is now withdrawn proximally (arrow 316) by the practitioner to aspirate (arrow 318) supposed venous blood 320. By aspirating blood, a fresh supply is slowly passed through the catheter lumen 230 between the LED array 144 and photodetector 170. Light emitted from the LEDs is received by the detector with appropriate levels of absorption from which the oxygen saturation of the hemoglobin therein may be calculated.

Note that, in another embodiment, the introduction needle 120 can be withdrawn partially so as to expose the array 144 and photodetector 170, with the conformance between the needle shaft and inner lumen of the catheter 110 forming a fluid seal. This is a simpler technique, as attachment of a new separate syringe (310) is not required. The introduction needle's syringe base is provided with a plunger 240 (FIG. 2) that allows aspiration of blood.

Figure 5:
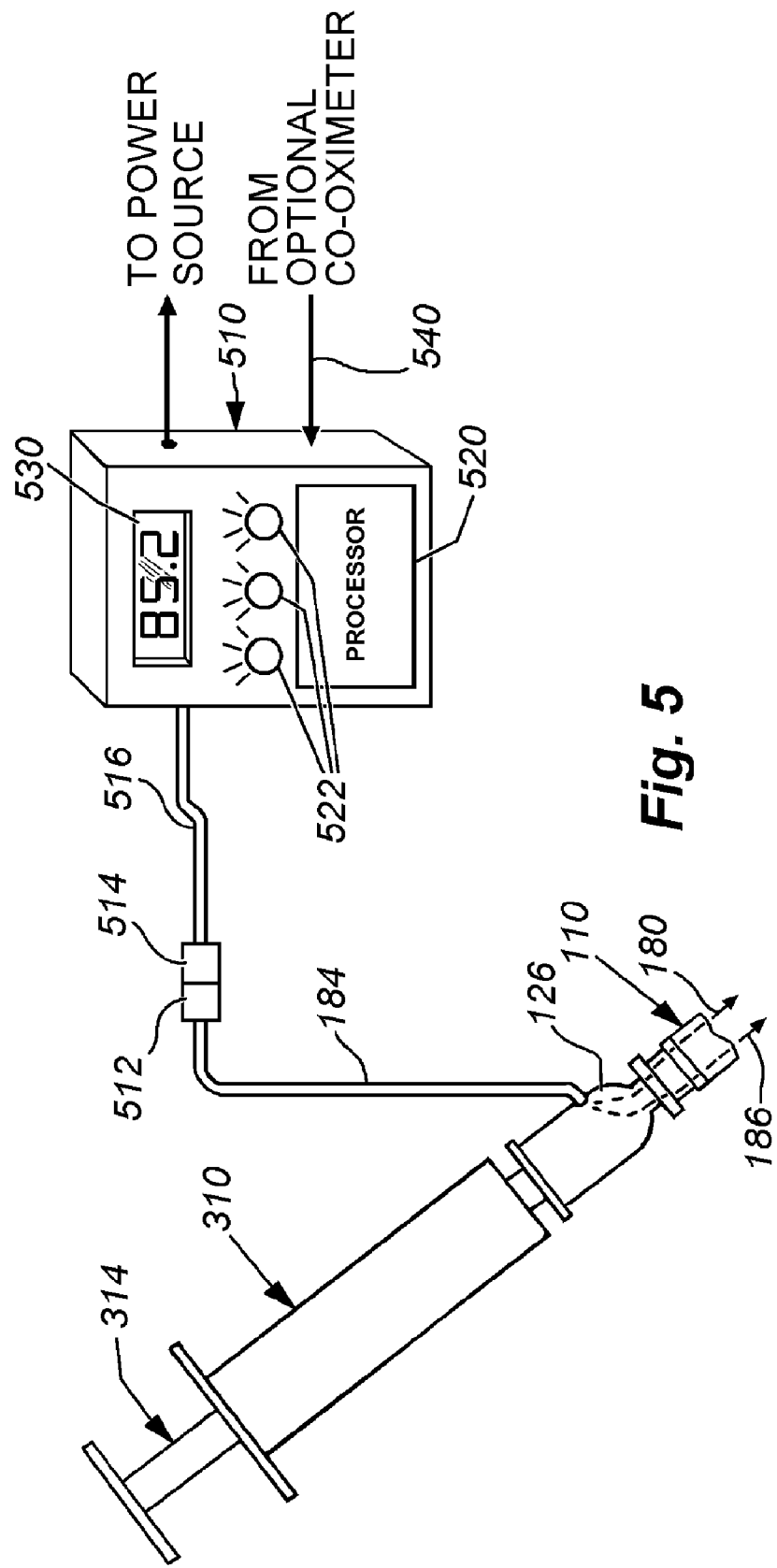
FIG. 5 is a partial perspective view of the proximal end of the catheter of FIG. 1 interconnected with an exemplary oximetry data display device according to an illustrative embodiment.

Referring to FIG. 5, the calculation of oxygen saturation level is performed by a powered base unit 510 that is interconnected with the catheter 110 when a reading of saturation level is desired. Appropriate, mating connectors 512 and 514 are provided on the catheter cable 184 and base unit cable 516, respectively. The length of each cable is highly variable. In one embodiment, the catheter 110 contains a cable having a length of approximately 300-500 mm and the base unit 510 has a cable of approximately 1-2 meters. One of the cables can be omitted in favor of a device mounted connector. In most embodiments, the single-use nature of the catheter 110 and multi-use nature of the base unit 510 make a removable connection desirable. The connector can be a conventional multi-pin male/female connector, or another desirable type that is capable of providing multiple lead connections. Within the base unit is a processor 520 that is activated by various switches and activates appropriate status lights (show generally as items 522). The processor provides power to the LEDs in the array 144 and photodetector 170 so that absorption of light therebetween can be measured.

Using the above-described Beer-Lambert relationship, the processor 520 employs conventional algorithms to calculate the measured oxygen saturation level. In one implementation, each LED 140, 142 is alternately cycled (multiple times per second, for example), and the processor differentiates between pulses received from each LED wavelength to calculate the saturation level. The processor 520 can comprise a variety of implementations of hardware, software (program instructions executing on a computer) and firmware. It can include one or more microprocessors, microcontrollers and/or state machines that carry out the required algorithms. The processor and its functions can be implemented according to ordinary skill using well-known circuit and software design techniques. In one example, the processor can be similar in structure and function to any one of a number of commercially available pulse oximetry and/or $SjVO_2$ monitoring devices.

Optionally, the signal from a connected (connection 540) co-oximeter can be employed to provide a value for arterial blood saturation against which the measured value of the catheter-derived value is compared. This co-oximeter can be a peripheral, non-invasive pulse oximeter of conventional design (not shown). The processor is adapted, using known circuits and processes, to recognize and correlate the co-oximeter's measured value. The measured saturation values derived from the catheter are, thus, scaled in accordance with the input co-oximeter value.

The processor 520 uses other known procedures and circuits to provide the value to a display 530. The display 530 can include a numeric readout as shown, which provides the actual saturation level as a percentage, or in accordance with another metric. In addition, or alternatively, the display can provide a simple go/no-go indicator that indicates whether the saturation level comports with venous or arterial blood. As discussed above, a saturation percentage that is near or into the 90s indicates the presence of arterial blood (ostensibly present due to a puncture or misdirected needle), while a measured saturation percentage at or below the mid-80s indicates venous blood without a suspected puncture.

Figure 6:
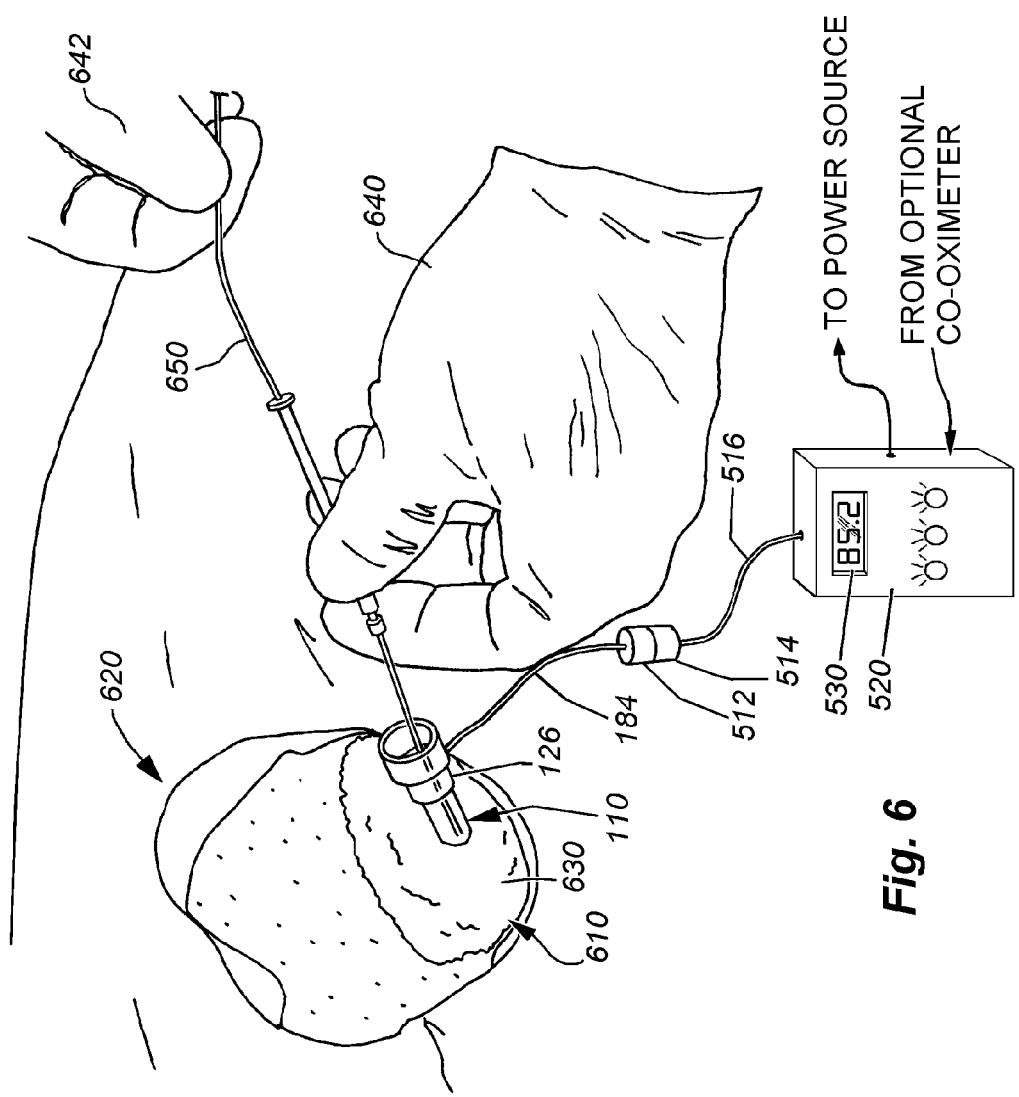
FIG. 6 is a perspective view of a procedure for inserting a guidewire into the catheter of FIG. 1 following the withdrawal on the introduction needle.

Thus, the practitioner is provided with a highly reliable, internally derived indication as to whether arterial cannulation has occurred based upon the displayed saturation level. If cannulation has occurred, standard pressure is applied to the area to shunt any bleeding and a new attempt is made to acquire a proper vein. Notably, the small diameter of the catheter 110 and introduction needle 120 generally limit the potential for arterial damage and excessive bleeding. As discussed above, that damage would be far greater if a full-sized CVC were subsequently introduced to the improper area.

Where the display 530 indicates that proper vein acquisition has occurred, the practitioner can now employ the catheter 110 to insert a conventional guide wire as shown in FIG. 6. A sterile field is provided at the introduction area 610, with a drape 620 provided therearound. The hub 126 of the catheter 110 rests on the skin 630 thereby interfering with further distal movement of the catheter 110 into the vein. The hub 126 can be further secured with sterile tape or another removable mechanism. The syringe 310 has been removed, opening the catheter lumen to the interior of the vein. At this time the practitioner manipulates (with hands 640, 642) a small-diameter guidewire 650 through the catheter lumen and into the vein via the proximal end of the hub 126. At some time before or during this stage of the procedure, the catheter connector 512 can be disconnected from the base unit connector 514.

Figure 7:
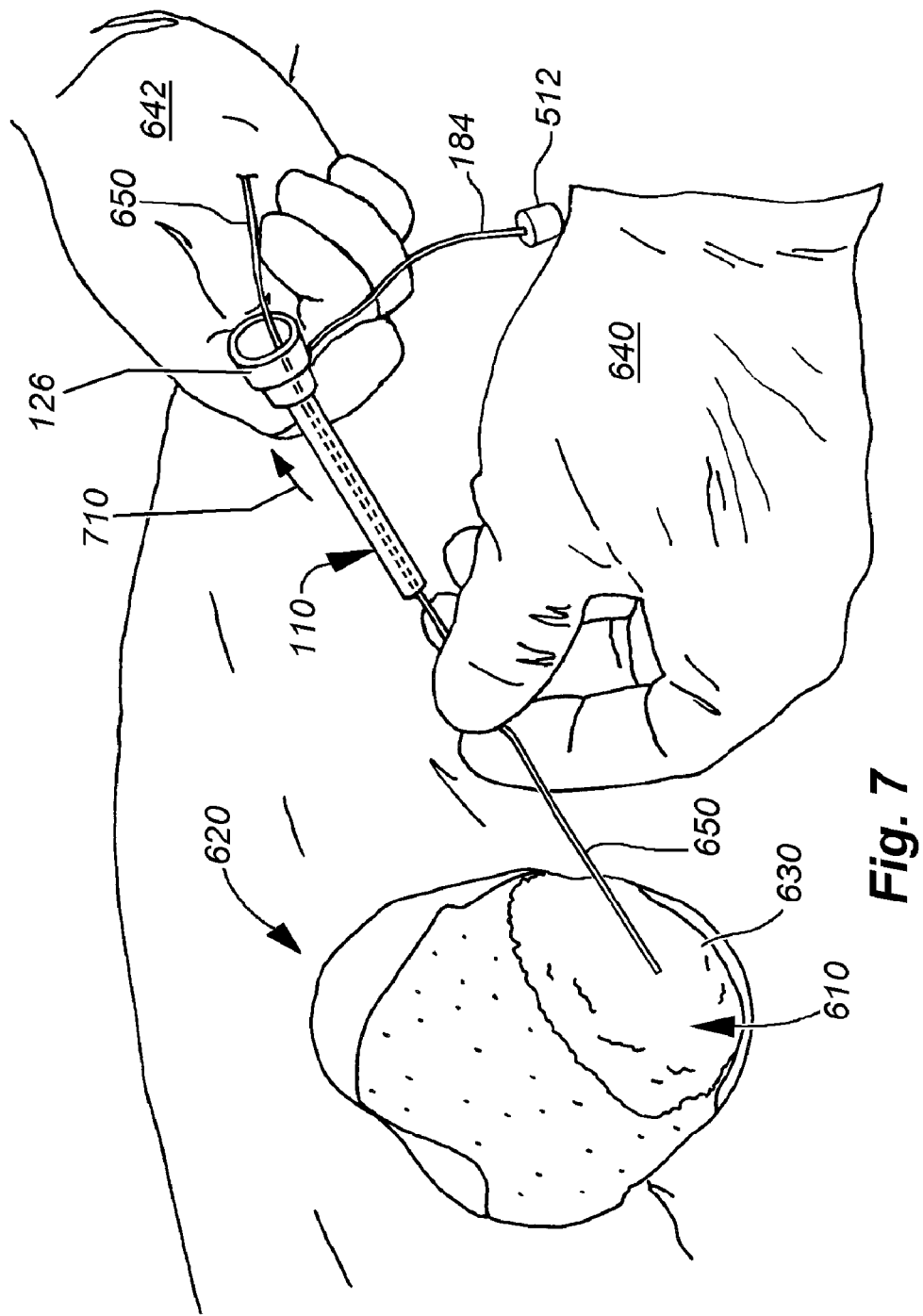
FIG. 7 is a perspective view of a procedure for removing the catheter of FIG. 1 along the inserted guidewire of FIG. 6.

Next, as shown in FIG. 7, the catheter 110 is removed from the site 610 by drawing it proximally (arrow 710) along the guidewire 650 while the guidewire is held firmly in place within the vein. The catheter 110 is drawn completely off the proximal end of the guidewire 650, thereby freeing the guidewire for insertion of a larger diameter catheter.

Figure 8:
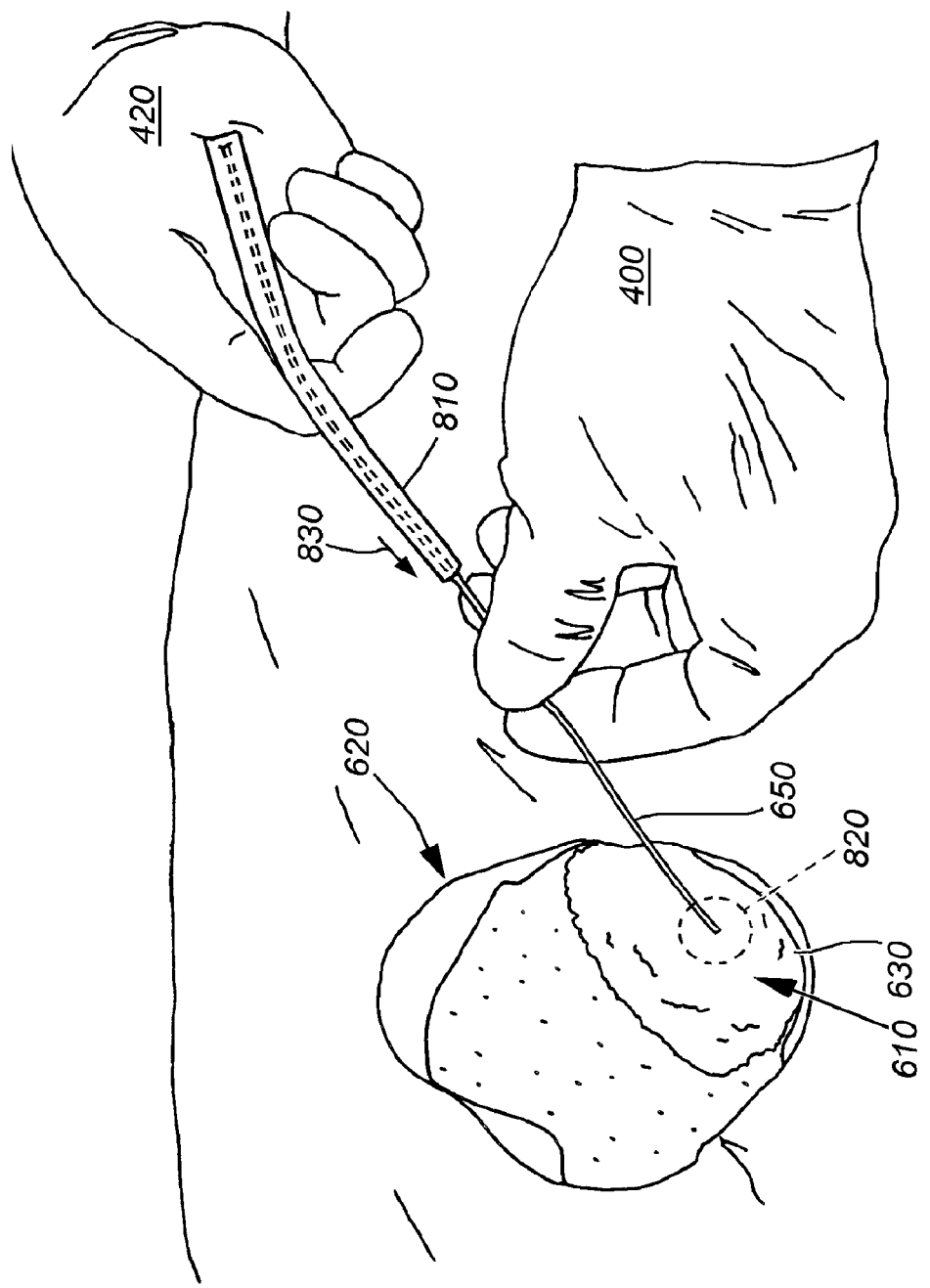
FIG. 8 is a perspective view of the insertion of a large bore CVC along the guidewire of FIG. 6 following removal of the catheter of FIG. 1.

Referring now to FIG. 8, insertion of a full-sized CVC 810 along the guidewire 650 is detailed. While not shown, a dilator may be introduced beforehand along the guidewire to increase the size of the introduction site 820 (shown in phantom). The CVC, which can have a size of 8-9 French is now moved distally (arrow 830) along the guidewire. It is inserted through the introduction site and driven into the vein until it reaches the appropriate location therein. The CVC can then be secured to the skin 630 using tape and other mechanisms so as to perform its needed function (i.e. nutrition, medication monitoring, and the like). The guidewire is then removed.

C. Extended Oximetry Catheter

Figure 9:
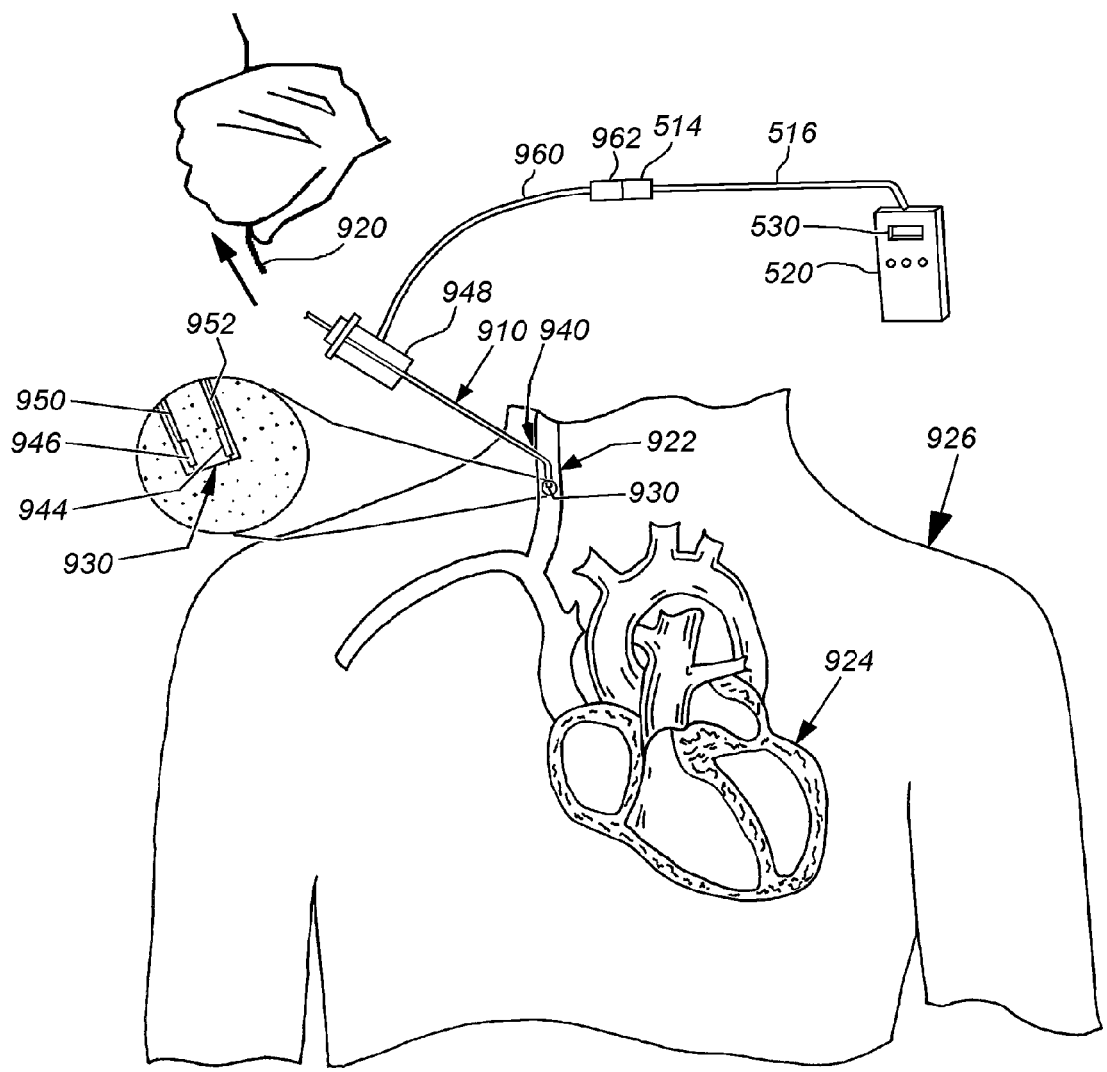
FIG. 9 is an exposed front view of the insertion of an elongate flexible venous oximetry catheter via a guidewire according to an alternate embodiment.

With reference to FIG. 9, according to an alternate embodiment, an oximetry catheter 910 that is adapted to be guided via a previously inserted (now removed) guide wire 920 is shown. The guide wire can comprise a conventional steerable or unsteered guide wire. The catheter 910 is longer and sufficiently flexible to allow it to be inserted more deeply into a vessel 922 of the central circulatory system (in closer proximity to the cardiopulmonary system) 924 of the body 926. In this manner the distal tip 930 can be located further from a convenient insertion site 940 to provide desired date on oxygen saturation. This data can be used to confirm lack of arterial cannulation prior to replacement of the guidewire and insertion thereon of a CVC. Alternatively, the catheter 910 can be used to monitor oxygen saturation on a more permanent basis. The distal tip 930 contains an LED array 944 and photodetector 946 similar or identical to those (144, 170) described above for the catheter 110. These sensing elements 944, 946 are connected to the hub 948 by embedded leads 944, 946. The hub is connected to a cable 960 and associated connector 962. The connector can mate with the above-described base unit connector 514 or another monitoring device that performs a similar measurement and display function. The materials used to construct the distal shaft and hub of this catheter are typically polymer, and can be adapted to provide needed flexibility over a long length. The diameters and thickness of the catheter 910 can be similar to those of the above-described catheter 110 or differ as needed for the particular application.

D. Oximetry Catheter with Remote Sensing Bulb

Figure 10:
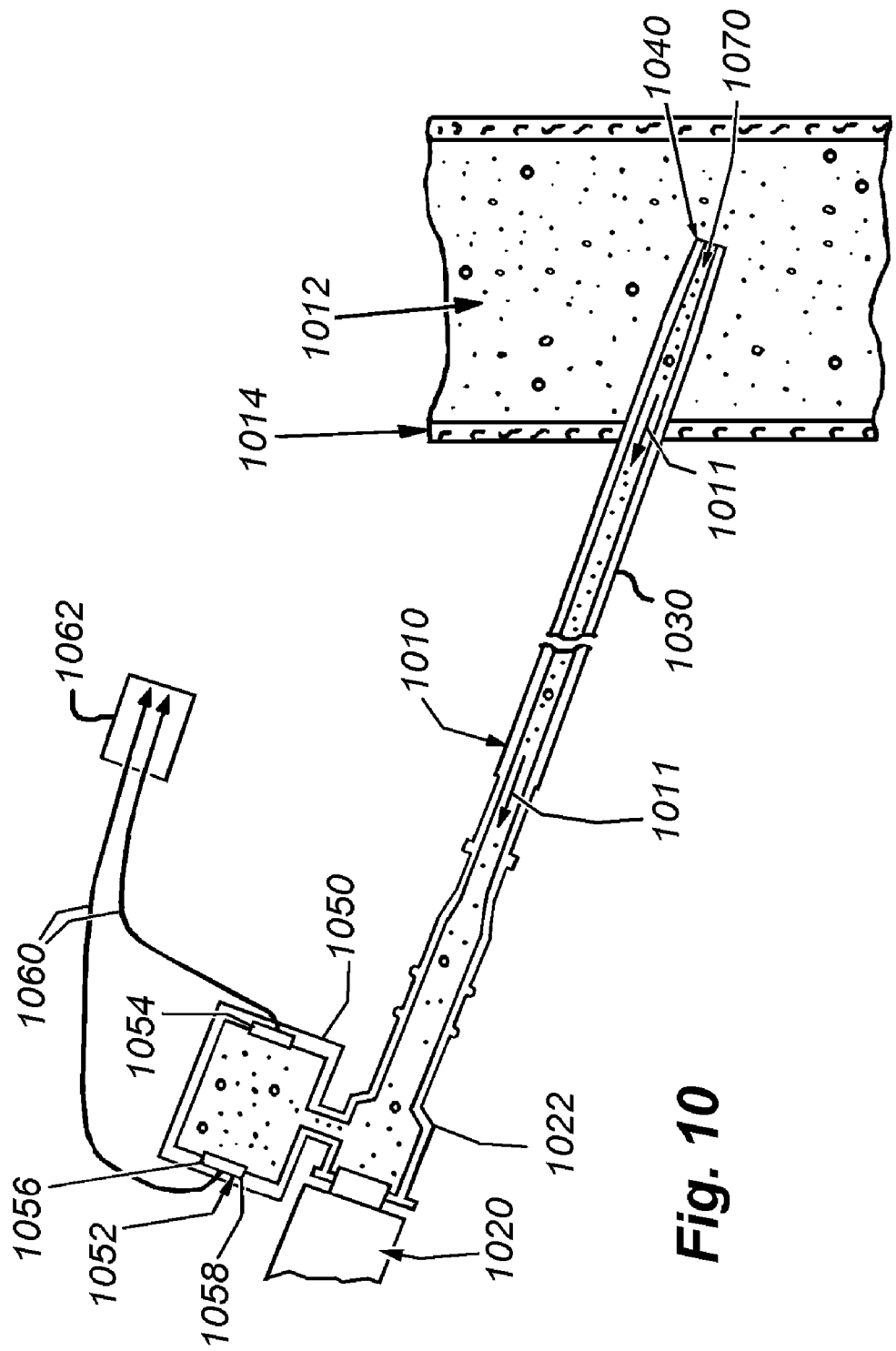
FIG. 10 is an exposed side view of a central venous oximetry catheter employing an external oximetry sensing cell according to an alternate embodiment of this invention.

In accordance with the alternate embodiment shown in FIG. 10, it is contemplated that the sensing elements can be placed external of the body and still attain a good result, provided the aspirated blood remains free of oxygen. In this embodiment, the catheter 1010 draws (arrows 1011) blood from the bloodstream 1012 of a supposed vein 1014 using a syringe 1020. The syringe is connected in a fluid-tight arrangement to the catheter hub 1022. The size and shape of the catheter shaft 1030 and hub 1022 can be similar or identical to those of the above-described catheter 110. It can be introduced using a needle similar to the introduction needle 120 described above. In this embodiment, the distal tip 1040 is free of sensing devices. Rather, the sensing devices are provided in a sealed bulb in communication with the hub. This enables use of a larger scale LED array 1052, consisting of at least two discrete LED units 1056 and 1058 each emitting a corresponding discrete wavelengths. A larger scale photodetector 1054 is diametrically opposed to the array 1052 in the bulb 1050 and receives the absorbed light therefrom. The elements 1052, 1054 are connected via cabling 1060 to a connector 1062 that can interconnect with a base unit such as the above described unit 520. In a further embodiment, within the above-described extended catheter 910, provided with external sensing elements similar in spectrophotometric principle, but utilizing differing wavelengths as previously described, the sensing window is useful to ascertain concentrations of blood constituents, including but not limited to solutes, electrolytes, complex molecules, and pharmacologic agents. Accordingly, the external sensing elements 1052, 1052, disposed within a proximal end of the catheter, such as a remote sensing bulb, can measure absorption of light by the blood passing between the light emitter and photodetector to determine the level of blood constituents. It is well established that different blood constituent levels can be measured by differing the wavelengths. These wavelengths can be ascertained using conventional techniques through trial and error experimentation.

While a separate bulb 1050 is used in this embodiment to house the sensing elements, these larger scale elements can also be located in the hub itself, or in a special syringe body according to further embodiments. As in the above-described embodiment, a guidewire and CVC can be subsequently inserted using the lumen 1070 of this catheter 1010.

Note that the above-described extended catheter 910 can be provided with external sensing elements similar to those described herein as opposed to the depicted distal-tip-mounted elements.

E. General Conclusions and Considerations

It should be clear that the above-described embodiments each desirably employ concepts of oximetry, with relatively direct sensing of venous blood at the site of CVC placement, to ensure avoidance of arterial cannulation. A variety of arrangements can be employed to such perform the sensing, either within the vein interior, or at a remote location still relatively proximate thereto. The catheter used for accessing the bloodstream is relatively small in diameter and less potentially damaging than a conventional CVC, thereby lowering the risks associated with initial acquisition of the vein. The small-diameter catheter then enables the guidance of larger-diameter (and potentially more damaging) structures to a confirmed safe location within a vein.

The foregoing has been a detailed description of a plurality of embodiments of the invention. Various modifications and additions can be made without departing from the spirit and scope thereof. In an alternate embodiment, some or all of the electrical components can be external. According to such an example, the leads for the emitters and detectors can be substituted with small-diameter light-waveguides and the emitters and detectors can be waveguide tips. The external cable is a fiber optic that connects to a base unit with a fiber optic-to-electric-signal interface. In addition, in alternate embodiments, it is contemplated that the LED array can include light transmitted in three or more wavelengths for better resolution. Each wavelength can be transmitted and sensed as a separate pulse in a continuous cycle. Also, while a particular insertion procedure for the oximetry catheter and CVC is shown and described herein, this procedure can be varied or augmented as need to satisfy the needs of the treatment protocol, practitioner or patient. Accordingly this description is meant to be taken only by way of example, and not to otherwise limit the scope of the invention.

What is claimed is:

1. A system for determining constituents of blood in a vascular region comprising:
   a small diameter catheter adapted to be introduced to the vascular region using an introduction needle over which the catheter is mounted, the catheter including a distal shaft defining a lumen and a hub;
   a light emitter and a photodetector constructed and arranged to pass light through blood from the emitter to the photodetector when the blood is drawn through the lumen and into the hub from the vascular region; and
   a processor operatively connected to at least one of the light emitter and the photodetector that measures and indicates a level of blood constituents of the blood drawn from the vascular region;
   wherein the light emitter and photodetector are both positioned on a surface of the lumen, such that when the blood is drawn through the lumen, the light passes from the light emitter through the blood in the lumen to the photodetector, to allow measurement of light absorbed by the blood moving between the light emitter and the photodetector as blood is drawn through the lumen.

2. The system as set forth in claim 1 wherein the lumen is adapted to receive a guide wire and is in a range of approximately 1 mm in diameter.

3. The system as set forth in claim 2 wherein further comprising leads embedded in the shaft and extending to a cable and connector that extends remotely from a location proximate to the hub.

4. The system as set forth in claim 2 wherein the light emitter comprises a micro LED assembly located within the lumen proximate to the distal tip of the catheter and the photodetector comprises a miniature photodetector located within the lumen diametrically opposed to the LED assembly.

5. The system as set forth in claim 4 wherein the LED assembly comprises LEDs that emit light in at least two discrete ranges of wavelengths at predetermined times.

6. The system as set forth in claim 5 wherein the discrete ranges of wavelengths comprise the infra red band and the visible red light band.

7. The system as set forth in claim 2 wherein the processor is constructed and arranged to receive a signal from a co-oximeter and to compare a value for oxygen saturation from the co-oximeter to a measured value based upon the light emitter and the photodetector.

8. The system as set forth in claim 2 wherein the light emitter and the photodetector are located at a position in fluid communication with the lumen that is external to a vascular region.

9. The system as set forth in claim 8 wherein the light emitter and the photo detector are located in a structure proximate to the hub.

10. The system as set forth in claim 1 wherein the level of blood constituents is determined for at least one of solutes, electrolytes, complex molecules, and pharmacologic agents.

11. A method for introducing a central venous catheter (CVC) to a vascular region comprising the steps of:
- introducing a small diameter catheter that is mounted on an introducer needle, through tissue and into the vascular region;
- removing the needle so as to place a light emitter and a photodetector in communication with a lumen of the catheter, a distal tip of the lumen being located within the vascular region;
- aspirating blood through the lumen so as to pass between the light emitter and photodetector;
- measuring absorption of light by the blood passing between the light emitter and the photodetector such that when the blood is drawn through the lumen, the light passes from the light emitter through the blood in the lumen to the photodetector, so as to determine a level of blood constituents of the blood moving within the lumen, between the light emitter and the photodetector; and
- when venous blood is detected, free of arterial blood, directing a guidewire through the lumen, removing the catheter and guiding a CVC over the guide wire into the vascular region.

12. The method as set forth in claim 11 further comprising analyzing a signal from a non-invasive co-oximeter to provide a comparison for the step of determining.

13. The method as set forth in claim 11 wherein the step of aspirating includes drawing blood with a syringe attached to a proximal hub of the catheter.

14. The method as set forth in claim 11 wherein the step of measuring includes emitting light from at least two discrete LED units that emit light at each of infra red range and a visible red range at predetermined times.

15. The method as set forth in claim 11 wherein the step of measuring absorption of light includes emitting light from at least two discrete LED units at two discrete wavelengths and measuring absorption of light by the blood passing between the light emitter and the photodetector and determining a level of blood constituents, including at least one of solutes, electrolytes, complex molecules, and pharmacologic agents.

16. The system as set forth in claim 1 wherein the light emitter and photodetector are disposed in opposed positions about the lumen.

17. The system as set forth in claim 1 wherein the light emitter and photodetector are disposed in diametrically opposed positions about the lumen.

18. The system as set forth in claim 1 wherein the light emitter comprises an LED assembly located within the lumen proximate to a distal tip of the catheter and the photodetector comprises a miniature photodetector located within the lumen diametrically opposed to the LED assembly.

19. The system as set forth in claim 18 wherein the LED assembly comprises LEDs that emit light in at least two discrete ranges of wavelengths at predetermined times.

20. The system as set forth in claim 19 wherein the discrete ranges of wavelengths comprise the infra red band and the visible red light band.

21. The system as set forth in claim 1 wherein the light emitter and the photodetector are located at a position in fluid communication with the lumen that is external to a vascular region.

22. The system as set forth in claim 21 including a separate sealed bulb in communication with the hub with the light emitters and photodetector provided at the sealed bulb.

23. The system as set forth in claim 22 wherein the photodetector is diametrically opposed to the light emitter, and the light emitter includes an LED array.

24. A system for measuring blood constituents in a vascular region comprising:
- a small diameter catheter adapted to be introduced to the vascular region using an introduction needle over which the catheter is mounted, the catheter including a distal shaft defining a lumen and a hub;
- a light emitter and a photodetector disposed proximate the hub of the catheter, the light emitter and the photodetector being constructed and arranged to pass light through blood from the emitter to the photodetector when the blood is drawn through the lumen and into the hub from the vascular region; and
- a processor operatively connected to at least one of the light emitter and the photodetector that measures and indicates a level of blood constituents of the blood drawn from the vascular region;
- wherein the light emitter and photodetector are positioned so that when the blood is drawn through the lumen, the light passes from the light emitter through the blood in the lumen to the photodetector, to allow measurement of light absorbed by the blood moving between the light emitter and the photodetector as blood is drawn through the lumen.

25. The system as set forth in claim 24 wherein the light emitter and photodetector are disposed proximate the hub of the catheter by means of a separate sealed bulb in communication with the hub.

26. The system as set forth in claim 25 wherein the light emitters and photodetector are provided at the sealed bulb.

27. The system as set forth in claim 26 wherein the photodetector is diametrically opposed to the light emitter, and the light emitter includes an LED array.

28. The system as set forth in claim 24 wherein the level of blood constituents is determined for at least one of solutes, electrolytes, complex molecules, and pharmacologic agents.

29. The method as set forth in claim 11 wherein the step of introducing a small diameter catheter that is mounted on an introducer needle includes providing the needle having a diameter of approximately 20 gauge.

30. The method as set forth in claim 11 wherein the step of determining the level of blood constituents includes determining for at least one of solutes, electrolytes, complex molecules, and pharmacologic agents.

* * * * *